United States Patent [19]

Preidel et al.

[11] Patent Number: 5,704,354
[45] Date of Patent: Jan. 6, 1998

[54] ELECTROCATALYTIC GLUCOSE SENSOR

[75] Inventors: Walter Preidel, Erlangen, Germany; Sebastian Proels, Chicago, Ill.

[73] Assignee: Siemens Aktiengesellschaft, München, Germany

[21] Appl. No.: 494,123

[22] Filed: Jun. 23, 1995

[30] Foreign Application Priority Data

Jun. 23, 1994 [DE] Germany .................. 44 22 068.5

[51] Int. Cl.$^6$ ...................................... A61B 5/00
[52] U.S. Cl. .................. 128/635; 204/403; 204/415
[58] Field of Search ......................... 128/635; 204/403, 204/415; 436/14; 422/82.01, 82.02, 82.03, 90

[56] References Cited

U.S. PATENT DOCUMENTS

4,477,314  10/1984  Richter et al. .
4,919,770   4/1990  Preidel et al. .

FOREIGN PATENT DOCUMENTS

0 539 814  5/1993  European Pat. Off. .

*Primary Examiner*—Jennifer Bahr
*Assistant Examiner*—Eric F. Winakur
*Attorney, Agent, or Firm*—Kenyon & Kenyon

[57] ABSTRACT

An electrocatalytic sensor in catheter type of construction for determining glucose in body fluids, especially in the blood, having the following features:

- a tubular body made of bio-compatible material that is subdivided into three sections,
- a sleeve-shaped reference electrode arranged between the first and the second, or between the second and the third section of the tubular body,
- a sleeve-shaped working electrode arranged—correspondingly—between the second and the third, or between the first and the second section of the tubular body, said working electrode having a slit extending in longitudinal direction over the full length,
- a hydrophilic membrane stretched over the working electrode whose ends are guided through the slit into the interior of the electrode and which is held in the slit by a wedge made of bio-compatible material,
- a counter-electrode which seals the one end of the tubular body, and
- lead wires to the electrodes arranged within the tubular body which are brought to the outside through the other end of the tubular body.

10 Claims, No Drawings

ELECTROCATALYTIC GLUCOSE SENSOR

BACKGROUND OF THE INVENTION

1. Field of the Invention

The invention relates to an electrocatalytic sensor of the catheter type of construction for determining glucose in bodily fluids, especially in the blood.

2. Description of Related Art

The measurement of the glucose concentration in body fluids, especially in the blood of patients, is an important task in medical technology, for example, in the treatment of diabetes. Usually enzyme sensors serve to determine glucose in which glucose oxidase is used and, either the hydrogen peroxide developing upon oxidation or the reduced oxygen content is determined electrochemically. However, because of the use of an enzyme, such sensors do not exhibit the long-term stability required. Namely, the implantation duration of two years called for in medicine cannot be achieved with today's conventional technology.

Also known are sensors for determining glucose in which the electrochemical oxidation of the glucose serves as a measuring signal (see European Patent 0 101 880 and European Patent 0 103 109). These sensors, which in general are constructed as a flow cell, were tested successfully in experimental measurements in animals. In so doing, the measuring cell is integrated into a large vessel, in particular the carotid artery, by means of a vessel prosthesis. But this method is less suitable for clinical application, i.e., as routine treatment of patients. In this case, a catheter-type sensor construction should be used instead.

Electrocatalytic sensors are also already described as catheter sensors (European Laid-Open Print 0 539 814). But since such sensors have a membrane, tubular, bio-compatible membranes with long-term stability would be necessary for their realization. However such membranes with the required geometry, i.e., having a wall thickness of 10 to 40 μm and a diameter of 1 to 3 mm, are not obtainable.

SUMMARY OF THE INVENTION

The object of the invention is to specify an implantable—in blood vessels or subcutaneously—electrocatalytic glucose sensor in a catheter type of construction which can be produced in a simple manner and which has the long-term stability necessary for an implant.

This is achieved according to the invention by a sensor which is characterized by
- a tubular body made of bio-compatible material that is subdivided into three sections,
- a sleeve-shaped reference electrode arranged between the first and the second, or between the second and the third section of the tubular body,
- a sleeve-shaped working electrode arranged—correspondingly—between the second and the third, or between the first and the second section of the tubular body, said working electrode having a slit extending in longitudinal direction over the full length,
- a hydrophilic membrane stretched over the working electrode whose ends are guided through the slit into the interior of the electrode and which is held in the slit by a wedge made of bio-compatible material,
- a counter-electrode which seals the one end of the tubular body, and
- lead wires to the electrodes arranged within the tubular body which are brought to the outside through the other end of the tubular body.

DETAILED DESCRIPTION OF THE INVENTION

A subdivided tubular body serves for the construction of the catheter sensor according to the invention, the working electrode and the reference electrode being arranged between the individual sections. For that purpose, the tubular sections are slipped in each case over the upper and the lower edge of the sleeve or hollow cylinder-shaped electrodes and bonded to them. At one end, the tube is sealed by the counter-electrode. For that purpose, this electrode is designed as a tip electrode which is bonded to the end of the corresponding tube section. In this way the three electrodes—isolated from each other—are arranged side by side in the catheter sensor, and specifically in the order of counter-electrode/reference electrode/working electrode or counter-electrode/working electrode/reference electrode.

The counter-electrode is preferably a vitreous carbon electrode, especially in activated form; in addition, carbon, titanium, platinum and gold are also possible as materials for the counter-electrode. Platinum serves preferably as the material for the working electrode, i.e., the working electrode has the shape of a metal sleeve made of platinum; in addition, this electrode can consist, for example, of a platinum/iridium alloy. The surface of the working electrode is advantageously sand-blasted. The reference electrode is generally a silver/silver chloride electrode (Ag/AgCl). For that purpose, a metal sleeve made of silver is used which is sand-blasted and superficially chlorinated.

The tubular body of the catheter sensor is composed of bio-compatible material for which preferably silicone is used; but in addition, other suitable materials are also possible, in particular polyurethane. The tubular body generally has a diameter approximately between 1 and 3 mm. The individual tube sections are, for example, 20 mm, 5 mm and >300 mm long. The metal sleeves have a diameter corresponding to that of the tube sections. The electrodes are, for example, 10 mm (platinum sleeve) and 5 mm (silver sleeve) long. Overall, the catheter sensor has a length approximately between 30 and 80 cm. The tubular body or the catheter can be filled with plastic material such as silicone which, for example, is carried out by injecting an adhesive. In so doing, at least all inner electrode surfaces should be covered with silicone in order to be protected from water.

All the electrodes are contacted to a metal wire or a metal litz wire, made in particular of silver. These lead wires are brought out through the open end of the catheter and connected to an attachment plug. A shrink tube is slipped over the end of the catheter and the attachment plug so that the junction between tube and attachment plug is protected.

The essential component of the catheter sensor according to the invention is the working electrode provided with a hydrophilic membrane. This electrode consists of a hollow cylinder made of metal or rather of a metal sleeve which has a slit extending in longitudinal direction over the full length, i.e., is quasi cut-open in longitudinal direction. This slit serves for the simple and problem-free application and securing of an areal membrane. This membrane has a length that is greater than the circumference of the cylinder and a width that is less than the height of the cylinder.

To apply on the working electrode, one of the broadsides of the membrane is inserted through the longitudinal slit in the cylinder and the membrane is then guided around the outer cylinder envelope. Then the other broad end of the membrane is likewise guided through the slit, i.e., into the interior of the cylinder. Using a wedge made of bio-compatible material, in particular silicone, whose length corresponds approximately to the width of the membrane, the membrane is subsequently held fast in the longitudinal slit and stretched tightly over the cylinder surface. The cylinder surface remaining free at the two ends of the cylinder is used for bonding with the tube sections and for sealing.

Foreign substances which can adversely influence the determination of glucose are supposed to be kept away from the electrode by means of the membrane arranged on the working electrode. For that purpose, a hydrophilic membrane is used which generally has a thickness <50 µm; preferably, the membrane thickness is 10 to 40 µm. Advantageously, the membrane consists of polytetrafluoroethylene that has been made hydrophilic; but in addition, other materials well tolerated by the body are also possible, for example sulphonated polysulphone.

The electrical triggering of the electrocatalytic glucose sensor according to the invention takes place in a generally known manner, for which the method known from the European Patent 0 101 880 serves in particular. In this case, a potential varying per unit time in potential steps of 150 mV is impressed on the working electrode within the potential range between 1 and 1650 mV, measured against the reversible hydrogen electrode (duration each time: 10 s); the potential step at 1650 mV lasts 30 s. An a.c. voltage is superimposed on this potential, measurement being made at each potential step at two frequencies (for example at 999 Hz and 4.5 Hz) and the real and imaginary portion of the impedance of the working electrode being determined. From these values a calibration vector is ascertained and with that the glucose concentration is calculated.

What is claimed is:

1. A catheter type electrocatalytic sensor for determining glucose in body fluids, comprising a tubular body of bio-compatible material that is subdivided into a first section, a second section and a third section, a sleeve-shaped reference electrode arranged between the first and the second, or between the second and the third section of the tubular body, a sleeve-shaped working electrode arranged—correspondingly—between the second and the third, or between the first and the second section of the tubular body, said working electrode having a slit extending in a longitudinal direction over its full length, a hydrophilic membrane stretched over the working electrode having ends which extend through the slit into the interior of the electrode and which is held in the slit by a wedge made of bio-compatible material, a counter-electrode which seals a first end of the tubular body, and lead wires to the electrodes arranged within the tubular body and which extend outside the tubular body through a second end of the tubular body.

2. The sensor according to claim 1, wherein the tubular body is filled at least partially with plastic material.

3. The sensor according to claim 1, wherein at least one of the bio-compatible material and the plastic material is silicone.

4. The sensor according to claim 1, wherein the tubular body has a diameter of from about 1 mm to about 3 mm.

5. The sensor according to claim 1, wherein the working electrode is composed of platinum.

6. The sensor according to claim 1, wherein the membrane is composed of hydrophilized polytetrafluoroethylene.

7. The sensor according to claim 1, wherein the membrane has a thickness of from about 10 µm to about 40 µm.

8. The sensor according to claim 1, wherein the counter-electrode is composed of vitreous carbon.

9. The sensor according to claim 1, wherein the reference electrode is a silver/silver chloride electrode.

10. The sensor according to claim 1, wherein the sensor has a length of from about 30 cm to about 80 cm.

* * * * *